(12) United States Patent
Rosinko (10) Patent No.: US 10,279,105 B2
(45) Date of Patent: May 7, 2019

(54) SYSTEM AND METHOD FOR MODIFYING MEDICAMENT DELIVERY PARAMETERS AFTER A SITE CHANGE

(71) Applicant: Tandem Diabetes Care, Inc., San Diego, CA (US)

(72) Inventor: Michael Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 848 days.

(21) Appl. No.: 14/581,398

(22) Filed: Dec. 23, 2014

(65) Prior Publication Data

US 2015/0182693 A1    Jul. 2, 2015

Related U.S. Application Data (60) Provisional application No. 61/920,923, filed on Dec. 26, 2013.

(51) Int. Cl.
  *A61M 31/00* (2006.01)
  *A61M 5/142* (2006.01)
  (Continued)

(52) U.S. Cl.
  CPC .... *A61M 5/14244* (2013.01); *A61M 5/16831* (2013.01); *A61M 5/172* (2013.01);
  (Continued)

(58) Field of Classification Search
  CPC .... A61M 2005/14208; A61M 2205/50; A61M 2205/52; A61M 5/14244; A61M 5/16831; A61M 5/172
  See application file for complete search history.

(56) References Cited

U.S. PATENT DOCUMENTS

| 5,080,653 A | 1/1992 | Voss et al. |
| 5,851,197 A | 12/1998 | Marano et al. |

(Continued)

FOREIGN PATENT DOCUMENTS

| WO | WO 2008103175 A1 | 8/2008 |
| WO | WO 2008144693 A1 | 11/2008 |

(Continued)

OTHER PUBLICATIONS

YiM. Luijf, Dissertation, "Closing the Loop, Squaring the Circle: Studies on Insulin Delivery, Glucose Monitoring and the Artificial Pancreas," Ch. 5, Fig. 2 at 62, University of Amsterdam 2013 (available at http://dare.uva.nl/record/452204), 12 pages.

*Primary Examiner* — Rebecca E Eisenberg
(74) *Attorney, Agent, or Firm* — Patterson Thuente Pedersen, P.A.

(57) ABSTRACT

Apparatuses and methods for delivery of medicaments such as insulin disclosed herein can increase the effectiveness of therapy by adjusting medicament delivery parameters to account for the loss of medicament absorption upon delivering medicament at a new insertion site. When a needle is inserted at a new site on a patient's body for delivery of medicament to that patient, a natural inflammatory response by the body to insertion of the needle causes the body to resist absorption of the delivered medicament. However, this medicament resistance decreases over time. Embodiments of the invention therefore adjust medicament delivery to deliver less medicament as time passes after an infusion set change causes medicament to be delivered at a new insertion site.

24 Claims, 6 Drawing Sheets

(51) Int. Cl.
*A61M 5/168* (2006.01)
*A61M 5/172* (2006.01)
*G06F 19/00* (2018.01)
*G16H 40/63* (2018.01)

(52) U.S. Cl.
CPC .......... *G06F 19/00* (2013.01); *G06F 19/3468* (2013.01); *G16H 40/63* (2018.01); *A61M 2005/14208* (2013.01); *A61M 2205/50* (2013.01); *A61M 2205/52* (2013.01)

(56) References Cited

U.S. PATENT DOCUMENTS

| | | | |
|---|---|---|---|
| 6,056,718 A | 5/2000 | Funderburk et al. |
| 6,248,093 B1 | 6/2001 | Moberg |
| 6,251,098 B1 | 6/2001 | Rake et al. |
| 6,461,329 B1 | 10/2002 | Van Antwerp et al. |
| 6,520,938 B1 | 2/2003 | Funderburk et al. |
| 6,558,320 B1 | 5/2003 | Causey, III et al. |
| 6,558,351 B1 | 5/2003 | Steil et al. |
| 6,572,586 B1 | 6/2003 | Wojcik |
| 6,585,695 B1 | 7/2003 | Adair et al. |
| 6,641,533 B2 | 11/2003 | Causey, III et al. |
| 6,652,493 B1 | 11/2003 | Das |
| 6,744,350 B2 | 6/2004 | Blomquist |
| 6,752,785 B2 | 6/2004 | Van Antwerp et al. |
| 6,852,104 B2 | 2/2005 | Blomquist |
| 6,926,694 B2 | 8/2005 | Marano-Ford et al. |
| 6,991,619 B2 | 1/2006 | Marano-Ford et al. |
| 6,991,620 B2 | 1/2006 | Marano-Ford et al. |
| 7,022,108 B2 | 4/2006 | Marano-Ford et al. |
| 7,033,338 B2 | 4/2006 | Vilks et al. |
| 7,041,082 B2 | 5/2006 | Blomquist et al. |
| 7,052,483 B2 | 5/2006 | Wojcik |
| 7,128,730 B2 | 10/2006 | Marano-Ford et al. |
| 7,214,207 B2 | 5/2007 | Lynch et al. |
| 7,267,665 B2 | 9/2007 | Steil et al. |
| 7,291,126 B2 | 11/2007 | Shekalim |
| 7,303,543 B1 | 12/2007 | Maule et al. |
| 7,311,693 B2 | 12/2007 | Shekalim |
| 7,354,420 B2 | 4/2008 | Steil et al. |
| 7,361,155 B2 | 4/2008 | Sage, Jr. et al. |
| 7,390,314 B2 | 6/2008 | Stutz, Jr. et al. |
| 7,402,153 B2 | 7/2008 | Steil et al. |
| 7,407,490 B2 | 8/2008 | Bendsen et al. |
| 7,442,186 B2 | 10/2008 | Blomquist |
| 7,494,481 B2 | 2/2009 | Moberg et al. |
| 7,510,544 B2 | 3/2009 | Vilks et al. |
| 7,515,060 B2 | 4/2009 | Blomquist |
| 7,520,867 B2 | 4/2009 | Bowman et al. |
| 7,530,968 B2 | 5/2009 | Gonnelli |
| 7,628,772 B2 | 12/2009 | Mcconnell et al. |
| 7,628,782 B2 | 12/2009 | Adair et al. |
| 7,654,127 B2 | 2/2010 | Krulevitch et al. |
| 7,704,227 B2 | 4/2010 | Moberg et al. |
| 7,717,903 B2 | 5/2010 | Estes et al. |
| 7,785,313 B2 | 8/2010 | Mastrototaro |
| 7,794,426 B2 | 9/2010 | Briones et al. |
| 7,806,886 B2 | 10/2010 | Kanderian, Jr. et al. |
| 7,828,528 B2 | 11/2010 | Estes et al. |
| 7,833,196 B2 | 11/2010 | Estes et al. |
| 7,860,583 B2 | 12/2010 | Condurso et al. |
| 7,875,022 B2 | 1/2011 | Wenger et al. |
| 7,892,199 B2 | 2/2011 | Mhatre et al. |
| 7,905,859 B2 | 3/2011 | Bynum et al. |
| 7,938,797 B2 | 5/2011 | Estes |
| 7,944,366 B2 | 5/2011 | Krulevitch et al. |
| 7,946,985 B2 | 5/2011 | Mastrototaro et al. |
| 7,951,122 B2 | 5/2011 | Shekalim |
| 7,959,598 B2 | 6/2011 | Estes |
| 7,981,102 B2 | 7/2011 | Patel et al. |
| 7,981,105 B2 | 7/2011 | Adair et al. |
| 8,021,334 B2 | 9/2011 | Shekalim |
| 8,070,726 B2 | 12/2011 | Gonnelli et al. |
| 8,070,742 B2 | 12/2011 | Woo |
| 8,100,852 B2 | 1/2012 | Moberg et al. |
| 8,109,921 B2 | 2/2012 | Estes et al. |
| 8,127,046 B2 | 2/2012 | Grant et al. |
| 8,211,062 B2 | 7/2012 | Estes et al. |
| 8,221,385 B2 | 7/2012 | Estes |
| 8,234,126 B1 | 7/2012 | Estes |
| 8,250,483 B2 | 8/2012 | Blomquist |
| 8,277,435 B2 | 10/2012 | Estes |
| 8,285,328 B2 | 10/2012 | Caffey et al. |
| 8,287,495 B2 | 10/2012 | Michaud et al. |
| 8,298,184 B2 | 10/2012 | Diperna et al. |
| 8,340,792 B2 | 12/2012 | Condurso et al. |
| 8,344,847 B2 | 1/2013 | Moberg et al. |
| 8,346,399 B2 | 1/2013 | Blomquist |
| 8,348,886 B2 | 1/2013 | Kanderian, Jr. et al. |
| 8,348,923 B2 | 1/2013 | Kanderian, Jr. et al. |
| 8,385,972 B2 | 2/2013 | Bochenko et al. |
| 8,401,194 B2 | 3/2013 | Nierzwick et al. |
| 8,454,575 B2 | 6/2013 | Estes et al. |
| 8,454,576 B2 | 6/2013 | Mastrototaro et al. |
| 8,573,027 B2 | 11/2013 | Rosinko et al. |
| 8,986,253 B2 | 3/2015 | DiPerna |
| 2002/0065484 A1 | 5/2002 | Douglas et al. |
| 2002/0173769 A1 | 11/2002 | Gray et al. |
| 2003/0060765 A1 | 3/2003 | Campbell et al. |
| 2003/0163088 A1 | 8/2003 | Blomquist |
| 2003/0163789 A1 | 8/2003 | Blomquist |
| 2003/0216683 A1 | 11/2003 | Shekalim |
| 2004/0073095 A1 | 4/2004 | Causey et al. |
| 2005/0137530 A1 | 6/2005 | Campbell et al. |
| 2005/0143864 A1 | 6/2005 | Blomquist |
| 2006/0206054 A1 | 9/2006 | Shekalim |
| 2007/0088267 A1 | 4/2007 | Shekalim |
| 2007/0156033 A1 | 7/2007 | Causey, III et al. |
| 2007/0161955 A1 | 7/2007 | Bynum et al. |
| 2007/0167912 A1 | 7/2007 | Causey et al. |
| 2007/0179444 A1 | 8/2007 | Causey et al. |
| 2008/0045891 A1 | 2/2008 | Maule et al. |
| 2008/0071580 A1 | 3/2008 | Marcus et al. |
| 2008/0097309 A1 | 4/2008 | Enegren et al. |
| 2008/0125700 A1 | 5/2008 | Moberg et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0183060 A1 | 7/2008 | Steil et al. |
| 2008/0269714 A1 | 10/2008 | Mastrototaro et al. |
| 2008/0269723 A1 | 10/2008 | Mastrototaro et al. |
| 2008/0281276 A1 | 11/2008 | Shekalim |
| 2008/0294094 A1* | 11/2008 | Mhatre ............... A61M 5/1413 604/65 |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2009/0062767 A1 | 3/2009 | Van Antwerp et al. |
| 2009/0067989 A1 | 3/2009 | Estes et al. |
| 2009/0069745 A1 | 3/2009 | Estes et al. |
| 2009/0088731 A1 | 4/2009 | Campbell et al. |
| 2009/0156990 A1 | 6/2009 | Wenger et al. |
| 2009/0163855 A1 | 6/2009 | Shin et al. |
| 2009/0270833 A1 | 10/2009 | DeBelser et al. |
| 2009/0275887 A1 | 11/2009 | Estes |
| 2010/0049164 A1 | 2/2010 | Estes |
| 2010/0094251 A1 | 4/2010 | Estes |
| 2010/0114015 A1 | 5/2010 | Kanderian, Jr. et al. |
| 2010/0168538 A1 | 7/2010 | Keenan et al. |
| 2010/0168670 A1 | 7/2010 | Srisathapat et al. |
| 2010/0174266 A1 | 7/2010 | Estes |
| 2010/0228186 A1 | 9/2010 | Estes et al. |
| 2010/0249706 A1 | 9/2010 | Clemente |
| 2010/0262078 A1 | 10/2010 | Blomquist |
| 2010/0286467 A1* | 11/2010 | Pesach ................. A61M 5/158 600/9 |
| 2010/0305545 A1 | 12/2010 | Kanderian, Jr. et al. |
| 2010/0324382 A1 | 12/2010 | Cantwell et al. |

(56) References Cited

U.S. PATENT DOCUMENTS

| | | |
|---|---|---|
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0050428 A1 | 3/2011 | Istoc |
| 2011/0060280 A1 | 3/2011 | Caffey et al. |
| 2011/0082439 A1 | 4/2011 | Wenger et al. |
| 2011/0105955 A1 | 5/2011 | Yudovsky et al. |
| 2011/0112504 A1 | 5/2011 | Causey et al. |
| 2011/0118662 A1 | 5/2011 | Mhatre et al. |
| 2011/0144586 A1 | 6/2011 | Michaud et al. |
| 2011/0144616 A1 | 6/2011 | Michaud et al. |
| 2011/0152757 A1 | 6/2011 | Beck et al. |
| 2011/0152770 A1 | 6/2011 | Diperna et al. |
| 2011/0152824 A1 | 6/2011 | Diperna et al. |
| 2011/0166544 A1 | 7/2011 | Verhoef et al. |
| 2011/0190694 A1 | 8/2011 | Lanier, Jr. et al. |
| 2011/0208155 A1 | 8/2011 | Palerm et al. |
| 2011/0224601 A1 | 9/2011 | Shekalim |
| 2012/0017688 A1 | 1/2012 | Shekalim |
| 2012/0029433 A1 | 2/2012 | Michaud et al. |
| 2012/0030610 A1 | 2/2012 | Diperna et al. |
| 2013/0053816 A1 | 2/2013 | DiPerna et al. |
| 2013/0131630 A1 | 5/2013 | Blomquist |
| 2013/0324824 A1* | 12/2013 | Kamath ............... A61B 5/0002 600/365 |
| 2013/0324928 A1 | 12/2013 | Kruse |
| 2013/0331790 A1 | 12/2013 | Brown et al. |
| 2014/0053816 A1 | 2/2014 | Czapka et al. |
| 2014/0054883 A1 | 2/2014 | Lanigan et al. |
| 2014/0276420 A1 | 9/2014 | Rosinko |
| 2014/0276423 A1 | 9/2014 | Lecanu-Fayet |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276574 A1 | 9/2014 | Saint |
| 2014/0378898 A1 | 12/2014 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0082188 A1 | 3/2016 | Blomquist et al. |

FOREIGN PATENT DOCUMENTS

| | | |
|---|---|---|
| WO | WO 2008144695 A1 | 11/2008 |
| WO | WO 2008144697 A1 | 11/2008 |
| WO | WO 2008144698 A1 | 11/2008 |
| WO | WO 2009032399 A1 | 3/2009 |
| WO | WO 2009032400 A1 | 3/2009 |

* cited by examiner

SYSTEM AND METHOD FOR MODIFYING MEDICAMENT DELIVERY PARAMETERS AFTER A SITE CHANGE

RELATED APPLICATION

The present application claims the benefit of U.S. Provisional Application No. 61/920,923 filed Dec. 26, 2013, which is incorporated herein in its entirety by reference.

FIELD OF THE INVENTION

The present invention relates to ambulatory infusions pumps and, more particularly, to modifying parameters of pump delivery of medicaments such as insulin based on a time of use of an injection site.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

Infusion pumps have been developed for the administration of insulin and/or other medicaments for those suffering from both type I and type II diabetes. Some pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. patent application Ser. No. 13/838,617, U.S. patent application Ser. No. 13/827,707 and U.S. Pat. No. 8,287,495, each of which is incorporated herein by reference.

Portable infusion pumps can deliver medicament to patients through infusion sets that include tubing extending from the pump and a cannula with an associated needle that penetrates the patient's skin at an infusion site to allow infusion of the medicament through the cannula and into the patient. If a patient leaves the needle injected at the injection site for too long a period of time, negative side effects such as infection, scarring and lumps due to build up of fatty tissue can result. Therefore, patients are often instructed to rotate injection sites to avoid or minimize side effects. Depending on the type of cannula used, the general physiological response of the patient, and other factors, the time between insulin site rotations can vary. Often, sites are rotated every 24-48 hours or every 48-72 hours. In addition, when the needle is first inserted at a particular site, the body has a natural inflammatory response. This inflammatory response can affect the body's absorption of insulin or other medicaments at the site.

SUMMARY OF THE INVENTION

Apparatuses and methods for delivery of medicaments such as insulin disclosed herein can increase the effectiveness of therapy by adjusting medicament delivery parameters to account for the loss of medicament absorption upon delivering medicament at a new insertion site. When a needle is inserted at a new site on a patient's body for delivery of, e.g., insulin to that patient, a natural inflammatory response by the body to insertion of the needle causes the body to resist absorption of the delivered insulin. However, this insulin resistance decreases over time. Embodiments of the invention therefore adjust insulin or other medicament delivery to deliver less insulin as time passes after an infusion set change causes insulin to be delivered at a new insertion site.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for modifying insulin or other medicament delivery parameters based on the amount of time that insulin has been injected at an injection site. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Figure 1:
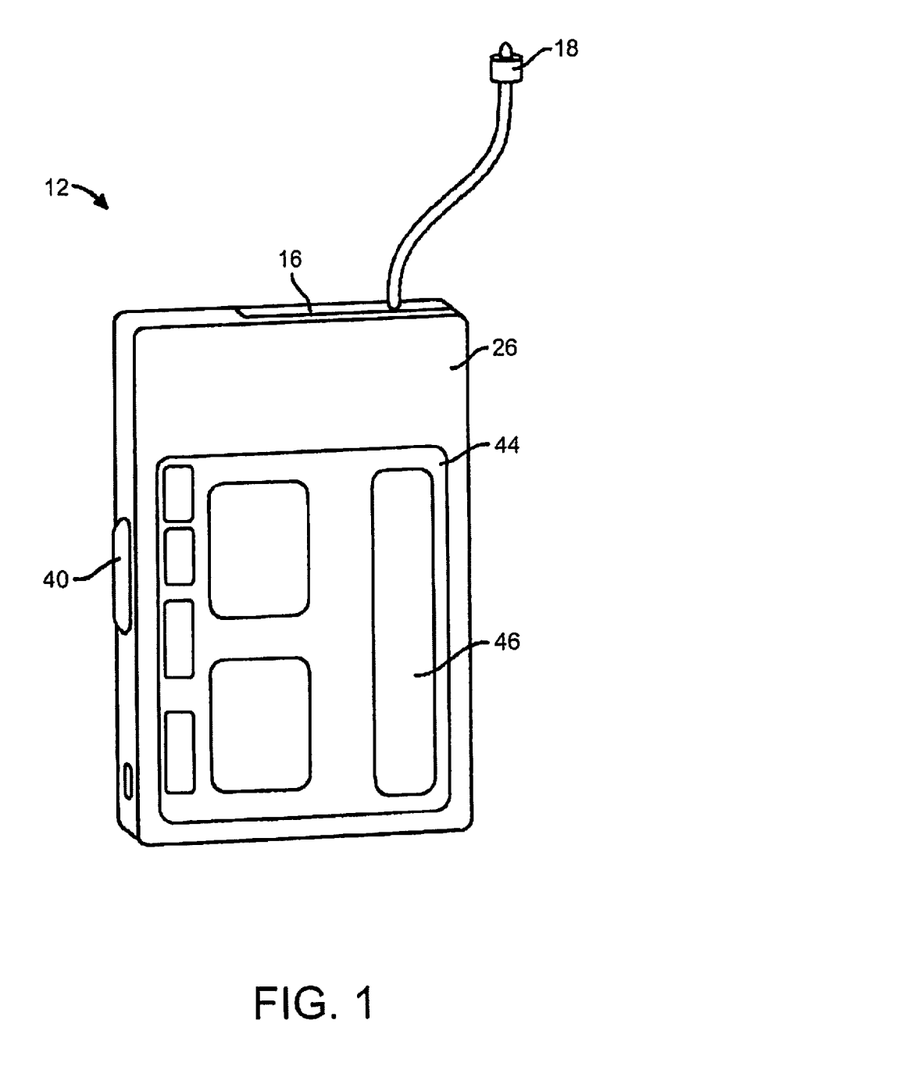
FIG. 1 is a perspective view of an infusion pump according to an embodiment of the present invention.

FIG. 1 depicts an embodiment of a pump 12 such as an infusion pump that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, grapheme-based displays, OLED displays and the like. The output/display 44 may also be an interactive or touch sensitive screen 46 having an input device such as, for example, a touch screen comprising a capacitive screen or a resistive screen. The pump 12 may additionally include a keyboard, microphone, or other input device known in the art for data entry, which may be separate from the display. Pump 12 may also include a capability to operatively couple to a secondary display device such as a remote display, a remote control device, a laptop computer, personal computer, tablet computer, mobile communication device such as a smartphone or personal digital assistant (PDA) or the like. Further details regarding such pump devices can be found in U.S. Patent Application No. 2011/0144586, which is incorporated herein by reference in its entirety.

Figure 2:
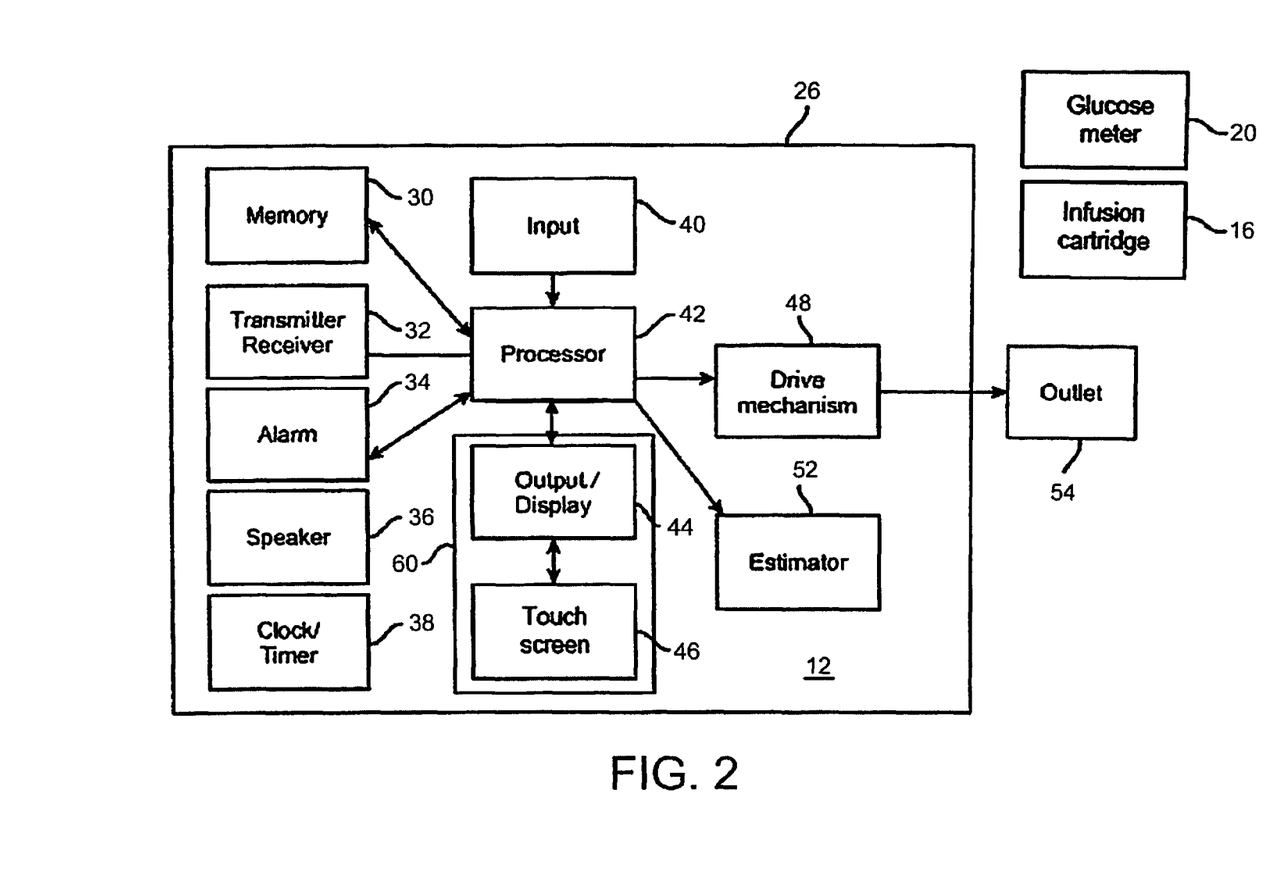
FIG. 2 is a block diagram representing an embodiment of an infusion pump according to the present invention.

FIG. 2 illustrates a block diagram of some of the features that can be used with embodiments of the present invention, including features that may be incorporated within the housing 26 of the pump 12. The pump 12 includes a processor 42 that functions to control the overall functions of the device. The infusion pump 12 may also include, e.g., a memory device 30, a communications device such as a transmitter/receiver 32, an alarm 34, a speaker 36, a clock/timer 38, an input device 40, the processor 42, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, transmitter/receiver and other components. In some embodiments, the processor 42 may communicate with another processor within the pump 12 and/or one or more processors of other devices, for example, a continuous glucose monitor (CGM), display device, smartphone, etc. through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature or other parameters. The processor 42 may determine the capacity of the drug delivery reservoir and/or the volume of fluid disposed in the drug delivery reservoir and may set therapeutic parameters based on its determination.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more templates or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual square wave, basal and bolus rate profiles, and/or the like. The memory can also store, for example, user information, history of use, glucose measurements, compliance and an accessible calendar of events. The memory can also store limits on insulin doses that can be delivered based on CGM data, as discussed herein.

The housing 26 of the pump 12 may be functionally associated with an interchangeable and removable glucose meter 20 and/or one or more infusion cartridges 16. The infusion cartridge 16 may have an outlet port 54 that may be connected to an infusion set (not shown in FIG. 1) via an infusion set connector 18.

Figure 3:
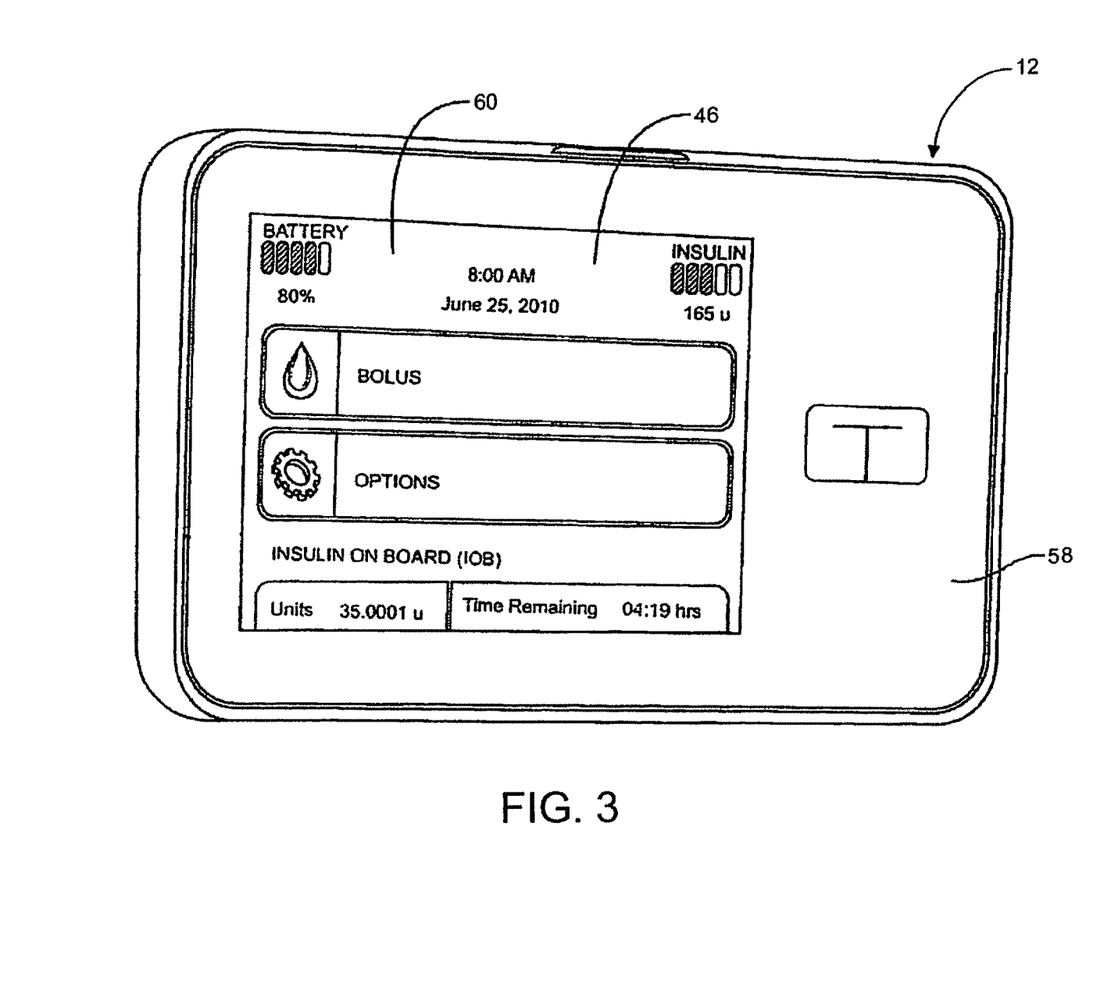
FIG. 3 depicts an exemplary screen shot of a home screen page of a graphical user interface of an infusion pump according to an embodiment of the present invention.

Referring to FIG. 3, a front view of a pump 12 is depicted. Pump 12 may include a user interface, such as, for example, a GUI 60 on a front surface 58 or other location of pump 12. GUI 60 may include a touch-sensitive screen 46 that may be configured for displaying data, facilitating data and/or command entry, providing visual tutorials, as well as other interface features that may be useful to a caregiver or to the patient operating pump 12. The GUI can also present alarms or alerts to the user.

Figure 4A:
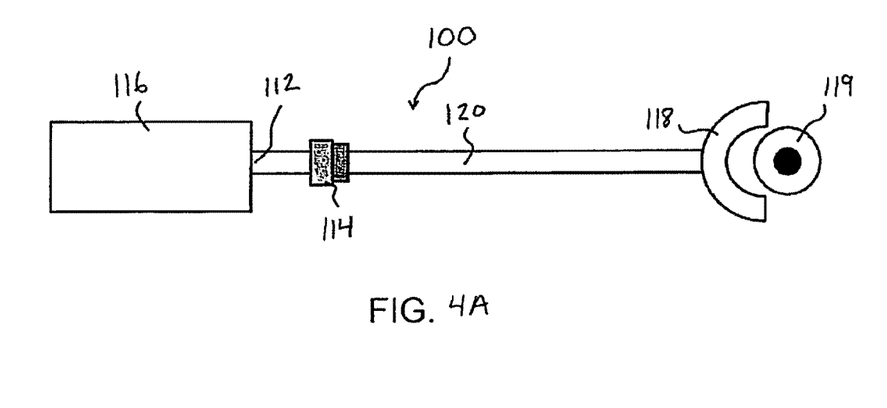
FIG. 4A depicts a schematic representation of an infusion set for use with an infusion pump according to an embodiment of the present invention.
Figure 4B:
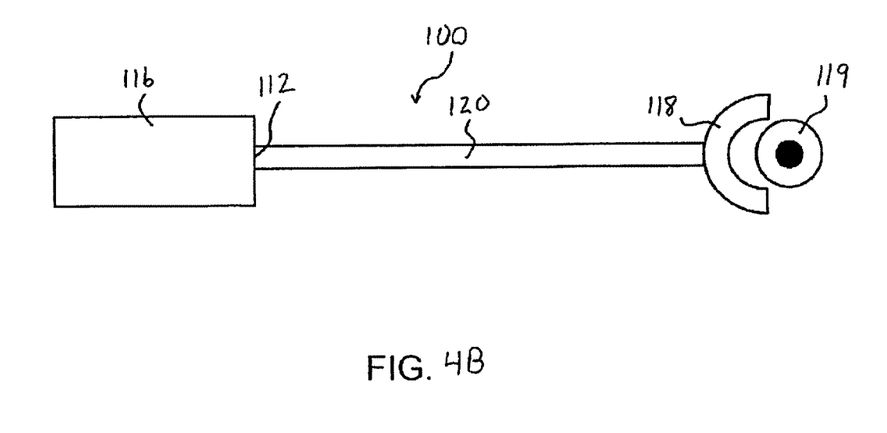
FIG. 4B depicts a schematic representation of an infusion set for use with an infusion pump according to an embodiment of the present invention.

FIGS. 4A and 4B depict embodiments of infusion sets 100 that can be used with infusion pumps as described herein to deliver medicament to a patient. Each infusion set can attach to one or more infusion cartridges, such as infusion cartridge 16 or 116. The infusion cartridge 116 can have one or more outlet ports or dispense ports 112 that can be connected to one or more infusion sets 100 at a proximal end of a length of tubing 120. The distal end of the length of tubing 120 can include a connector 118 that can attach or be pre-connected to a cannula and/or infusion needle that punctures the patient's skin at the infusion site 119. The tubing 120 is connected to the cannula with an inner lumen of the tubing 120 in fluid communication with an inner lumen of the cannula or infusion needle. In some embodiments, as shown in FIG. 4A, an infusion set connector 114 including a short length of tubing and a male lock fitting, such as a Luer lock fitting, can attach to a second length of tubing having a corresponding female lock fitting and the connector 118. In other embodiments, as shown in FIG. 4B, the infusion set 110 and corresponding tubing 120 can be preattached to the cartridge 116 such that the tubing 120 can extend from the port to the connector as a solid, uninterrupted and unitary piece of tubing with a constant diameter and having no connectors connecting portions of the tubing. Further details regarding examples of infusion sets that can be used in embodiments of the present invention can be found in U.S. Patent Application Publication No. 2014/0276423, which is hereby incorporated by reference in its entirety.

Figure 5A:
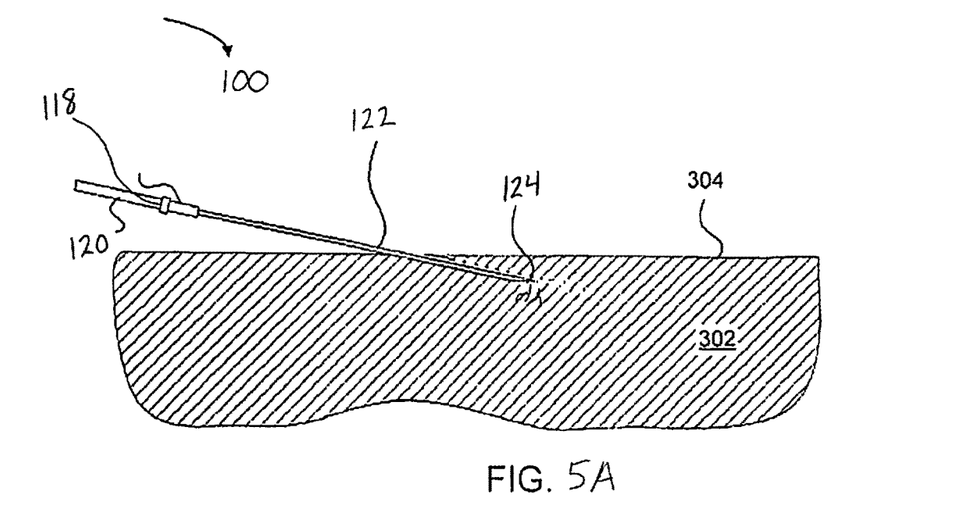
FIG. 5A depicts a schematic representation of a portion of an infusion set for use with an infusion pump according to an embodiment of the present invention inserted into a patient.
Figure 5B:
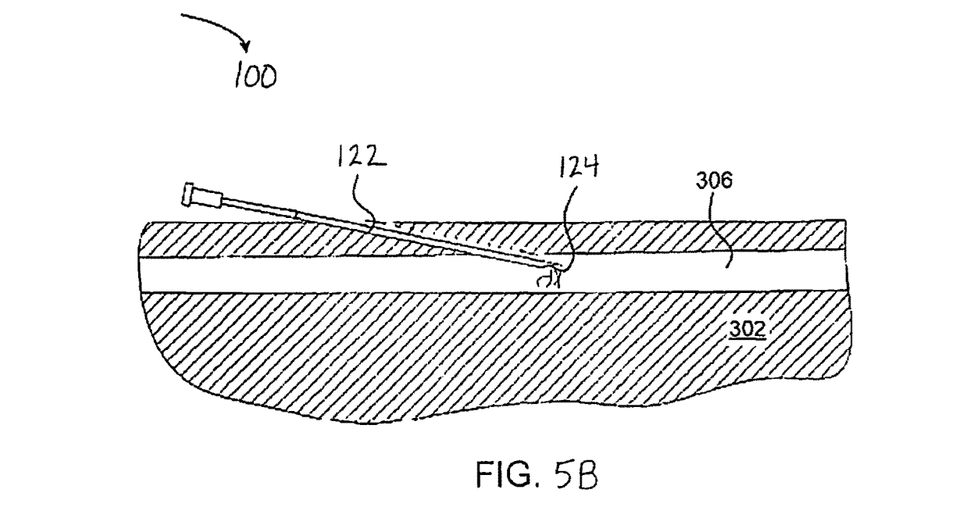
FIG. 5B depicts a schematic representation of a portion of an infusion set for use with an infusion pump according to an embodiment of the present invention inserted into a patient.

FIGS. 5A and 5B depict an infusion set 100 with a cannula 122 at a distal end of fluid tubing 120 of the infusion set 100 inserted into a patient's body 302 at an insertion site. The cannula 122 can be inserted in a subcutaneous space under the patient's skin 304 as shown in FIG. 5A. Alternatively, the cannula 122 can be disposed within an inner lumen of a patient's fluid vessel 306, such as shown in FIG. 5B. The infusion set 100 is in fluid communication with a dispense port of an infusion pump system, and fluids such as insulin and/or other suitable medicaments are shown being dispensed from an outlet port 124 of the cannula 122 and into the patient's body 302 at the insertion site. The distal end of the fluid tubing may be held in place by a piece of an adhesive pad (not shown in FIGS. 5A-5B) secured to the patient's skin 304.

Figure 6:
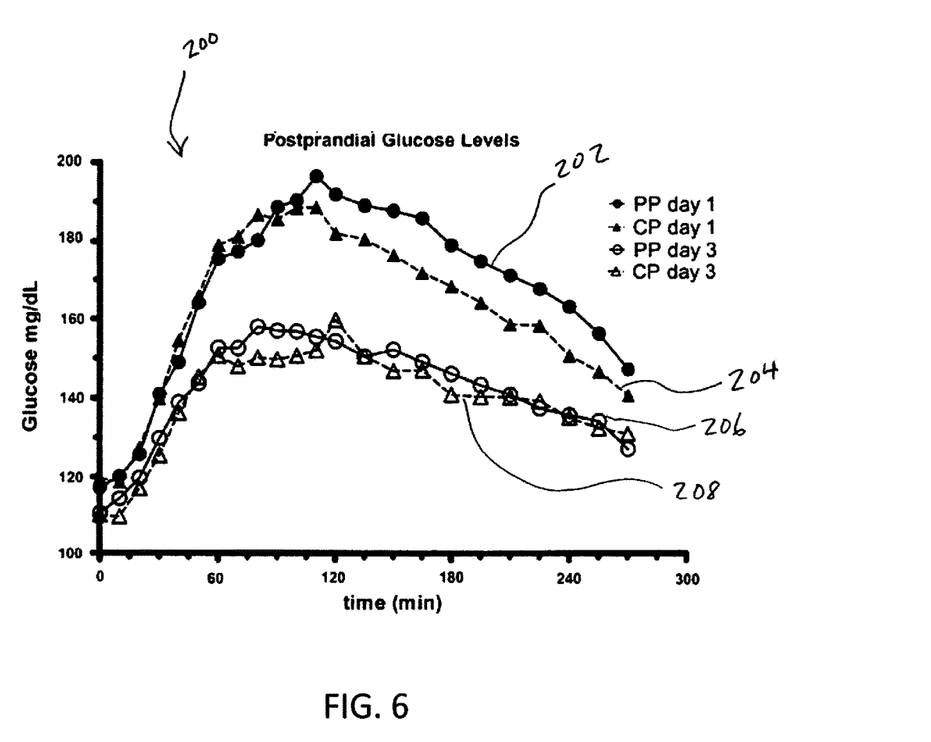
FIG. 6 is a graph showing mean postprandial blood glucose excursions for two days of patch pump and catheter pump use.

FIG. 6 is a graph 200 of mean sampled postprandial (after eating) blood glucose level excursions for two types of insulin pumps that depicts the change in insulin needs and absorption after an insertion site has been used for several days as reported in YiM. Luijf, Dissertation, "Closing the Loop, Squaring the Circle: Studies on Insulin Delivery, Glucose Monitoring and the Artificial Pancreas," Ch. 5, FIG. 2 at 62, University of Amsterdam 2013 (available at http://dare.uva.nl/record/452204), the entirety of which is hereby incorporated by reference. Line 202 represents mean sampled blood glucose level following administration of insulin after eating with a patch pump on a first day of use for an insertion site and line 204 illustrates the same with a conventional insulin pump for twenty (20) patients. Lines 206 and 208 depict postprandial response to insulin delivered with a patch pump and a conventional pump, respectively, on a third day of use for the insertion site. As can be seen by comparing line 202 with line 206 and line 204 with line 208, on the first day at the insertion site the subjects' mean sample blood glucose level rises higher and for a longer period of time for both types of pump before the blood glucose level begins to drop. The absolute value of the blood glucose level drop from the peak level is also comparatively greater. This may be due to an inflammatory response to the injection at the insertion site when the cannula is initially inserted, wherein such response provides resistance to the absorption of insulin at the insertion site. Over time, the inflammatory response and therefore the insulin resistance is believed to abate, enabling the body to more readily absorb the injected insulin. Thus, the longer an insertion site has been used, and other considerations notwithstanding, the less insulin a patient may need to effect the same treatment.

Embodiments of the invention seek to maximize the effectiveness of insulin and other medicament therapy by adjusting delivery parameters to account for the loss of medicament absorption upon delivering medicament at a new insertion site. The parameters can be adjusted to account for this effect by delivering less, e.g., insulin, the longer that an insertion site has been used. In some embodiments, the system can employ an algorithm that automatically adjusts medicament delivery parameters based on time of insertion. In certain embodiments, this automatic adjustment is an optional feature that can be turned on or off by a user.

In the context of insulin therapy, various insulin delivery parameters can be modified as time passes at a certain insertion site to account for changes in insulin absorption/needs. The modified parameter can be one or more of basal rate, insulin to carbohydrate ratio and insulin sensitivity, for example, as well as any other parameter that relates to or is involved in the calculation of the amount of insulin that is delivered to a patient. The basal rate can be decreased over time to directly result in less insulin being delivered. If the insulin to carbohydrate ratio is lowered as time passes, less insulin is delivered because a smaller amount of insulin will be calculated for delivery based on the number of carbohydrates consumed. The insulin sensitivity factor or correction factor could be increased over time to result in delivery of less insulin because a smaller amount of insulin would be needed to effect a blood glucose level reduction by the same or similar amount. In certain embodiments, the user can select one or more insulin delivery parameters that are modified based on time since the last infusion set change. Similar parameters can be modified for delivery of other medicaments.

The device can be programmed to automatically adjust these parameters over time. In one embodiment, one or more insulin delivery parameters can be at a first level on day 1 of use of an insertion site and adjusted by a fixed percentage to a different level on subsequent days. The parameter can be at its highest or lowest level the first day, whichever results in more insulin being delivered, and either lowered or raised the next day to deliver a smaller amount of insulin. In some embodiments, the parameter can be at the first level the first day and remain at a second level for all subsequent days that insulin is delivered at the same site. In other embodiments, the parameter can continue to be adjusted each subsequent day. The parameter can be adjusted by the same amount or percentage each day, or can be adjusted by a smaller amount or percentage each subsequent day to account for a smaller increase in insulin absorption each day. Although described with respect to adjustment of delivery by an amount or percentage each day, it should be understood that the time period for each adjustment can vary, such as, for example, every 12 hours. In some embodiments, the amount and/or percentage of modification as well as the time period can be adjusted by the user.

In another embodiment, the processor can execute an algorithm that gradually modifies the selected insulin delivery parameters over time. The parameter or parameters can begin at the time of an infusion set change at either a highest value or a lowest value and gradually be modified to decrease or increase to deliver smaller amounts of insulin. The modification can be done continually, i.e., the parameter is constantly changing as time passes, or periodically, i.e., the parameter is changed after regular intervals of time, such as, for example, every 30 minutes. The parameter(s) can be modified as a linear function over time. Alternatively, the parameter(s) can be modified as a nonlinear function over time. In some embodiments, a user can program and/or adjust each of the above aspects of the algorithm.

In some embodiments, the processor can alternatively or additionally adjust insulin or other medicament delivery to account for loss of insulin potency over time. After an insertion site has been used for a period of time, for example, the effect of insulin delivered at that site gradually decreases. Thus, the processor can alternatively or additionally automatically execute an algorithm that increases the delivery of insulin over time at a site. In one embodiment, following the site change the processor can reduce the delivery of insulin as described above to account for initial decreased absorption of insulin due to the inflammatory response at the site. After a certain amount of time in which it is estimated that the inflammatory response has or may have abated, insulin delivery can be increased over time to account for a decrease in insulin potency at the site. Alternatively, the processor can increase insulin delivery over time to account for a decrease in insulin potency without taking into account the inflammatory response.

In some embodiments, the processor of the insulin pump can automatically recognize that the infusion set has been changed and equate the change of the infusion set to delivery at a new insertion site. In one embodiment, the pump can include a sensor that senses that a first infusion set has been detached from the pump and therefore no longer in fluid communication with the pump and a second infusion set has subsequently been attached. Alternatively or in addition, the user can enter or confirm that a new insertion site is in use or that an infusion set has been changed on the user interface of the pump, and the processor can utilize that notification to determine that an infusion set has been detached and a new infusion set attached. It should be noted, however, that use of a new insertion site does not necessarily mean that a new infusion set has been attached. However, for purposes of adjusting delivery parameters over time, the processor can consider use of a new insertion site to be equivalent to use of a new infusion set.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230; 2013/0053816; 2013/0159456; 2013/0306191; 2013/0324928; 2013/0332874; 2013/0283196; 2013/0331790; 2013/0331778; 2014/0276531; 2014/0276419; 2014/0276420; 2014/0276423; 2014/0276,409; 2014/0276537; 2014/0276553; 2014/0276569; 2014/0276570; 2014/0276571; 2014/0276574; 2014/0276556; 2014/0276538; and commonly owned U.S. patent application Ser. Nos. 13/923,556; 14/479,994; and 14/482,521 and commonly owned U.S. Provisional Application Ser. Nos. 61/911,576, 61/920,902, 61/920,914, 61/920,932; 61/920,940; 61/990,501; and 62/030,933.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A portable infusion pump, comprising:
   a pump device configured to deliver medicament to a user through an infusion set in fluid communication with the pump device and physically connected to the user's body; and
   a processor communicatively coupled to the pump device to control the pump device to deliver the medicament to the user, the processor further configured to:
      determine that a first infusion set has been detached from fluid communication with the pump device and a second infusion set has subsequently been placed into fluid communication with the pump device;
      initiate delivery of medicament with the pump device through the second infusion set; and
      adjust delivery of medicament with the pump device through the second infusion set based on a time since initiating delivery of medicament through the second infusion set to account for changes in medicament absorption over time at an insertion site of the second infusion set.

2. The portable infusion pump of claim 1, wherein automatically adjusting delivery of medicament with the pump device based on a time since initiating delivery of medicament through the second infusion set includes reducing an amount of medicament delivered with the pump device as the time since initiating delivery increases.

3. The portable infusion pump of claim 1, wherein the processor is further configured to determine delivery of medicament with the pump device based on one or more medicament delivery parameters, and wherein automatically adjusting delivery of medicament with the pump device based on a time since initiating delivery of medicament includes adjusting a medicament delivery parameter.

4. The portable infusion pump of claim 3, wherein the medicament delivery parameter is a basal rate.

5. The portable infusion pump of claim 4, wherein automatically adjusting delivery of medicament includes decreasing the basal rate.

6. The portable infusion pump of claim 3, wherein the medicament delivery parameter is a carbohydrate ratio.

7. The portable infusion pump of claim 6, wherein automatically adjusting delivery of medicament includes decreasing the carbohydrate ratio.

8. The portable infusion pump of claim 3, wherein the medicament delivery parameter is an insulin sensitivity.

9. The portable infusion pump of claim 8, wherein automatically adjusting delivery of medicament includes increasing the insulin sensitivity.

10. The portable infusion pump of claim 1, further comprising a user interface, and wherein the processor is further configured to determine that the first infusion set has been detached from fluid communication with the pump device and the second infusion set has subsequently been placed into fluid communication with the pump device through an indication received through the user interface.

11. The portable infusion pump of claim 1, wherein the processor is configured to automatically determine that the first infusion set has been detached from fluid communication with the pump device and the second infusion set has subsequently been placed into fluid communication with the pump device.

12. The portable infusion pump of claim 1, wherein the medicament is insulin.

13. A portable infusion pump, comprising:
a cartridge including a reservoir of medicament and an outlet port selectively coupleable to an infusion set for delivery of the medicament to the user;
a pump device configured to selectively receive the cartridge, the pump device configured to selectively cause the medicament to be delivered from the reservoir through the infusion set to the user; and
a processor communicatively coupled to the pump device, the processor configured to:
determine that a first infusion set has been detached from the cartridge and a second infusion set has subsequently been placed into attached to the cartridge;
initiate delivery of medicament with the pump device through the second infusion set; and
adjust delivery of medicament with the pump device through the second infusion set based on a time since initiating delivery of medicament through the second infusion set to account for changes in medicament absorption over time at an insertion site of the second infusion set.

14. The portable infusion pump of claim 13, wherein automatically adjusting delivery of medicament with the pump device based on a time since initiating delivery of medicament through the second infusion set includes reducing an amount of medicament delivered with the pump device as the time since initiating delivery increases.

15. The portable infusion pump of claim 13, wherein the processor is further configured to determine delivery of medicament with the pump device based on one or more medicament delivery parameters, and wherein automatically adjusting delivery of medicament with the pump device based on a time since initiating delivery of medicament includes adjusting a medicament delivery parameter.

16. The portable infusion pump of claim 15, wherein the medicament delivery parameter is a basal rate.

17. The portable infusion pump of claim 16, wherein automatically adjusting delivery of medicament includes decreasing the basal rate.

18. The portable infusion pump of claim 15, wherein the medicament delivery parameter is a carbohydrate ratio.

19. The portable infusion pump of claim 18, wherein automatically adjusting delivery of medicament includes decreasing the carbohydrate ratio.

20. The portable infusion pump of claim 15, wherein the medicament delivery parameter is an insulin sensitivity.

21. The portable infusion pump of claim 20, wherein automatically adjusting delivery of medicament includes increasing the insulin sensitivity.

22. The portable infusion pump of claim 13, further comprising a user interface, and wherein the processor is further configured to determine that the first infusion set has been detached from fluid communication with the pump device and the second infusion set has subsequently been placed into fluid communication with the pump device through indication received through the user interface.

23. The portable infusion pump of claim 13, wherein the processor is configured to automatically determine that the first infusion set has been detached from fluid communication with the pump device and the second infusion set has subsequently been placed into fluid communication with the pump device.

24. The portable infusion pump of claim 13, wherein the medicament is insulin.

* * * * *